US012742768B2

(12) United States Patent
Boudjatit et al.

(10) Patent No.: US 12,742,768 B2
(45) Date of Patent: Sep. 22, 2026

(54) IN SITU CONCENTRATION OF HYDROCARBONS IN ROCK

(71) Applicant: SAUDI ARABIAN OIL COMPANY, Dhahran (SA)

(72) Inventors: Mohammed Boudjatit, El Kennar (DZ); Abdulhameed Azzouni, Dammam (SA); Ali Al Sultan, Dammam (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 414 days.

(21) Appl. No.: 18/477,226

(22) Filed: Sep. 28, 2023

(65) Prior Publication Data

US 2025/0110102 A1 Apr. 3, 2025

(51) Int. Cl.

*G01N 33/24* (2006.01)
*E21B 49/00* (2006.01)

(Continued)

(52) U.S. Cl.

CPC ........... *G01N 33/241* (2013.01); *E21B 49/00* (2013.01); *G01N 1/04* (2013.01); *G01N 15/088* (2013.01);

(Continued)

(58) Field of Classification Search

None

See application file for complete search history.

(56) References Cited

U.S. PATENT DOCUMENTS 9,507,047 B1 * 11/2016 Dvorkin ................. G01V 5/101
9,588,939 B2 * 3/2017 Buiting .................. G01V 11/00

(Continued)

FOREIGN PATENT DOCUMENTS

CN 113379209 A 9/2021
CN 113970512 A 1/2022

(Continued)

OTHER PUBLICATIONS

Bhosle, Balaji et al., "Effects of Sample Holding Time, Storage and Preservation on Sample Integrity for Source Rock Analysis: Experimental Results"; Proceedings of the SPE Asia Pacific Unconventional Resources Conference and Exhibition; Paper No. SPE-176973-MS; pp. 1-6; Nov. 9, 2015 (6 pages).

(Continued)

*Primary Examiner* — Raymond L Nimox

(74) *Attorney, Agent, or Firm* — Osha Bergman Watanabe & Burton LLP

(57) ABSTRACT

Methods and systems may include obtaining, from a rock coring system, rock samples, determining, using a nuclear magnetic resonance system, a hydrocarbon-filled porosity for each rock sample, determining, using a pyrolysis system, a concentration of hydrocarbons within each rock sample, and determining, using regression analysis, a relationship between the concentration of hydrocarbons and the hydrocarbon-filled porosity. The methods and systems may further include obtaining, from a well logging system, well logs along a well that penetrates an in situ rock, determining a total hydrocarbon-filled porosity for the in situ rock using the well logs, and obtaining the relationship. The methods and systems may still further include determining an in situ concentration of hydrocarbons within the in situ rock using the relationship and the total hydrocarbon-filled porosity and determining a recovery factor for the in situ rock based on the in situ concentration of hydrocarbons.

15 Claims, 10 Drawing Sheets

(51) Int. Cl.

| | |
|---|---|
| ***G01N 1/04*** | (2006.01) |
| ***G01N 15/08*** | (2006.01) |
| ***G01N 24/08*** | (2006.01) |
| ***G01N 25/20*** | (2006.01) |
| ***G01V 3/20*** | (2006.01) |

(52) U.S. Cl.
CPC ........... *G01N 24/081* (2013.01); *G01N 25/20* (2013.01); *G01V 3/20* (2013.01)

(56) References Cited

U.S. PATENT DOCUMENTS

2022/0237891 A1* 7/2022 Xu ........................ G06V 10/507
2023/0053348 A1 2/2023 Hu et al.

FOREIGN PATENT DOCUMENTS

CN 112487620 B 8/2022
CN 115112713 A 9/2022

OTHER PUBLICATIONS

Carvajal-Ortiz, Humberto et al., "High-frequency (20 MHz) NMR and Modified Rock-Eval Pyrolysis Methods as an Integrated Approach to Examine Producibility in Kerogen-Rich Source-Reservoirs"; Proceedings of the SPE/AAPG/SEG Unconventional Resources Technology Conference; Paper No. URTEC-2019-1005-MS; pp. 1-17; Jul. 22, 2019 (17 pages).

Michael, G.E. et al., "Determination of In-Situ Hydrocarbon Volumes in Liquid Rich Shale Plays"; Proceedings of the SPE/AAPG/SEG Unconventional Resources Technology Conference; Paper No. URTEC-1573030-MS; pp. 1-7; Aug. 12, 2013 (7 pages).

Downey, Marlan W. et al., "Quick Look Determination of Oil-in-Place in Oil Shale Resource Plays"; AAPG Annual Convention and Exhibition; Search and Discovery Article No. 40764; Jun. 30, 2011 (21 pages).

Zhi, Qi et al., "Correction of Light and Heavy Hydrocarbons and Their Application in a Shale Oil Reservoir in Gaoyou Sag, Subei Basin—A Case Study from Well SX84"; Processes; vol. 11, Issue 2, Article 572; pp. 1-12; Feb. 2023 (12 pages).

Minh, Cao et al., "2D-NMR Applications in Unconventional Reservoirs"; Proceedings of the SPE Canadian Unconventional Resources Conference; Paper No. SPE-161578-MS; pp. 1-17; Oct. 30, 2012 (17 pages).

Gorynski, K.E. et al., "Quantification and Characterization of Hydrocarbon-Filled Porosity in Liquid-Rich Shales using Basic Programed Thermal Extraction and Pyrolysis, LECO-TOC, Archimedes Bulk Density, and Helium Pycnometry Measurements"; Proceedings of the SPE/AAPG/SEG Unconventional Resources Technology Conference; Paper No. URTEC-2686515-MS; pp. 1-12; Jul. 24, 2017 (12 pages).

* cited by examiner

800 Obtain well logs along an interval of a well located within a subterranean region of interest, where the well penetrates an in situ rock of a rock type 805 Determine a total hydrocarbon-filled porosity for the in situ rock using, at least in part, the well logs 810 Obtain a relationship between a concentration of hydrocarbons and a hydrocarbon-filled porosity for the rock type 815 Determine an in situ concentration of hydrocarbons within the in situ rock using the relationship and the total hydrocarbon-filled porosity 820 Determine a recovery factor for the in situ rock based, at least in part, on the in situ concentration of hydrocarbons 825 Determine a hydrocarbon production rate based, at least in part, on the recovery factor 830 Design a production management plan based, at least in part, on the hydrocarbon production rate

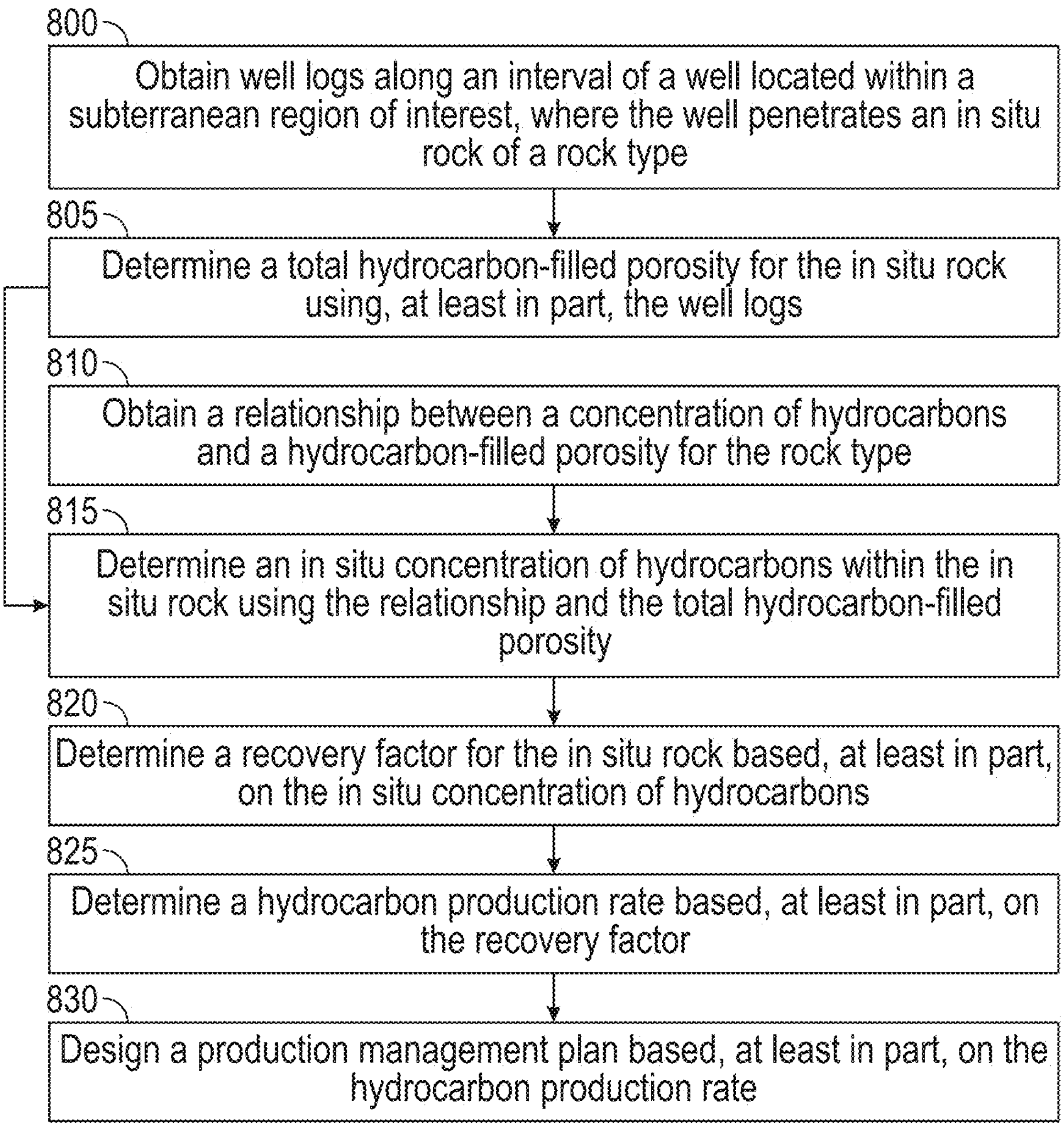

FIG. 8A

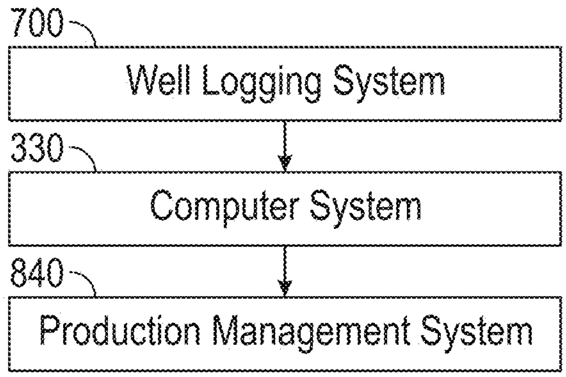

FIG. 8B

IN SITU CONCENTRATION OF HYDROCARBONS IN ROCK

BACKGROUND

A subterranean region of interest may be made up of layers of in situ rock, some of which may make up a hydrocarbon reservoir. The hydrocarbon reservoir may store hydrocarbons in various states. For example, the hydrocarbon reservoir may store free hydrocarbons and bound hydrocarbons. Free hydrocarbons may flow under normal hydrocarbon reservoir conditions. Bound hydrocarbons may not flow under normal hydrocarbon reservoir conditions. It may be advantageous to determine the concentration of free and bound hydrocarbons within the hydrocarbon reservoir prior to and/or during the extraction of those free and bound hydrocarbons to determine a hydrocarbon production rate.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In general, in one aspect, embodiments relate to a method. The method includes obtaining, from a rock coring system, rock samples and determining, using a nuclear magnetic resonance (NMR) system, a hydrocarbon-filled porosity for each of the rock samples. Each of the rock samples is of a rock type. The method further includes determining, using a pyrolysis system, a concentration of hydrocarbons within each of the rock samples and determining, using regression analysis, a relationship between the concentration of hydrocarbons and the hydrocarbon-filled porosity for the rock samples.

In general, in one aspect, embodiments relate to a method. The method includes obtaining, from a well logging system, well logs along an interval of a well located within a subterranean region of interest. The well penetrates an in situ rock within the subterranean region of interest at a discrete depth within the interval. The in situ rock is of a rock type. The method further includes determining a total hydrocarbon-filled porosity for the in situ rock using, at least in part, the well logs and obtaining a relationship between a concentration of hydrocarbons and a hydrocarbon-filled porosity for the rock type. The method still further includes determining an in situ concentration of hydrocarbons within the in situ rock using the relationship and the total hydrocarbon-filled porosity and determining a recovery factor for the in situ rock based, at least in part, on the in situ concentration of hydrocarbons.

In general, in one aspect, embodiments relate to a system. The system includes a computer system and a production management system. The computer system is configured to receive, from a well logging system, well logs along an interval of a well located within a subterranean region of interest. The well penetrates an in situ rock within the subterranean region of interest at a discrete depth within the interval. The in situ rock is of a rock type. The computer system is further configured to determine a total hydrocarbon-filled porosity for the in situ rock using, at least in part, the well logs and obtaining a relationship between a concentration of hydrocarbons and a hydrocarbon-filled porosity for the rock type. The computer system is still further configured to determine an in situ concentration of hydrocarbons within the in situ rock using the relationship and the total hydrocarbon-filled porosity and determine a recovery factor for the in situ rock based, at least in part, on the in situ concentration of hydrocarbons. The production management system is configured to determine a hydrocarbon production rate based, at least in part, on the recovery factor.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

FIG. 8A describes a method in accordance with one or more embodiments.

FIG. 8B shows a flowchart of systems in accordance with one or more embodiments.

DETAILED DESCRIPTION

Figure 1A:
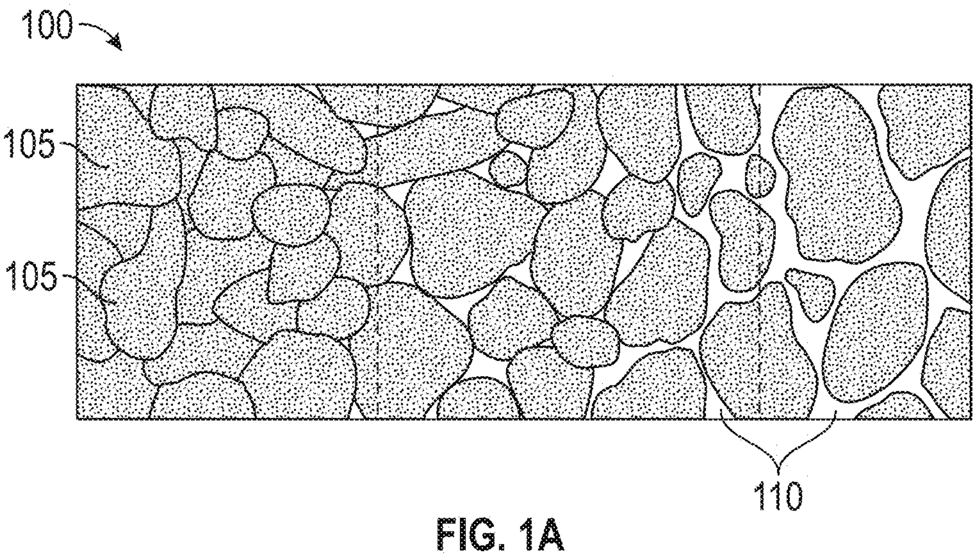
FIG. 1A illustrates rock in accordance with one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before," "after," "single," and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a rock sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowcharts may be omitted, repeated, and/or performed in a different order than the order shown. Accordingly, the scope disclosed herein should not be considered limited to the specific arrangement of steps shown in the flowcharts.

Although multiple dependent claims are not introduced, it would be apparent to one of ordinary skill in the art that the subject matter of the dependent claims of one or more embodiments may be combined with other dependent claims.

In the following description of FIGS. 1-11, any component described regarding a figure, in various embodiments disclosed herein, may be equivalent to one or more like-named components described regarding any other figure. For brevity, descriptions of these components will not be repeated regarding each figure. Thus, each and every embodiment of the components of each figure is incorporated by reference and assumed to be optionally present within every other figure having one or more like-named components. Additionally, in accordance with various embodiments disclosed herein, any description of the components of a figure is to be interpreted as an optional embodiment which may be implemented in addition to, in conjunction with, or in place of the embodiments described regarding a corresponding like-named component in any other figure.

Methods and systems are disclosed to determine an in situ concentration of hydrocarbons within in situ rock using a relationship. In some embodiments, the methods may be used to determine the in situ concentration of hydrocarbons within in situ rock. In other embodiments, the methods may be used to correct the concentration of hydrocarbons within an ex situ rock sample that may have lost free hydrocarbons following extraction from the in situ rock.

The methods disclosed herein may be considered an improvement over alternative methods that determine the in situ concentration of hydrocarbons within in situ rock and/or correct the concentration of hydrocarbons in an ex situ rock sample for at least one of the following reasons. Firstly, the disclosed methods may rely on a wide range of hydrocarbon constituents, such as light to medium to even heavy hydrocarbons, as opposed to alternative methods that rely on minimal hydrocarbon constituents, such as only $C_{15}$. Secondly, the disclosed methods may not rely on American Petroleum Institute (API) gravity measurements (a measure of relative density) as alternative methods do. Not relying on API gravity measurements may be advantageous as API gravity measurements may be prone to error. Thirdly, the disclosed methods may be applied to rock of the same rock type from any subterranean region of interest while alternative methods may only be applied to rock of the same rock type from one subterranean region of interest. As such, the disclosed methods may reduce the time and cost associated with extracting rock samples as the disclosed methods may rely on fewer rock samples compared to alternative methods.

FIG. 1A illustrates rock 100 in accordance with one or more embodiments. Rock 100 is composed of grains 105 that may be separated by space known as pores 110. The grains 105 may be a material made up of, but not limited to, quartz, calcite, or kerogen. The material of the grains 105 may be a key consideration in determining the rock type of the rock 100. FIG. 1A specifically illustrates rock 100 with various degrees of packing, with the packing decreasing from left to right. Packing, along with other structural properties of the grains 105 and pores 110, may control, at least in part, the porosity and permeability of the rock 100.

Figure 1B:
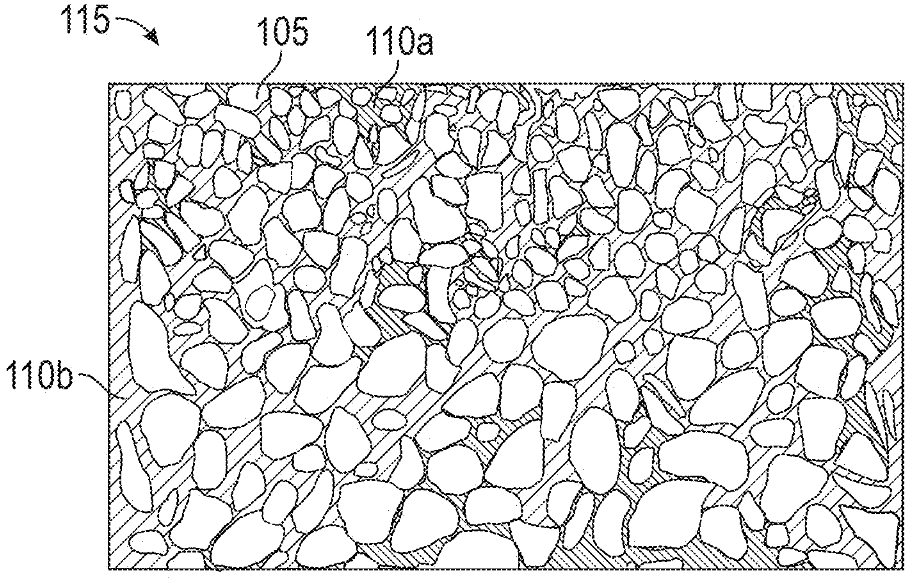
FIG. 1B illustrates fluid-filled rock in accordance with one or more embodiments.

Turning to FIG. 1B, FIG. 1B illustrates fluid-filled rock 115 in accordance with one or more embodiments. The fluid may be, but is not limited to, air, natural gas, water, brine, hydrocarbons, or any mixture thereof. FIG. 1B specifically shows pores 110 filled with water (hereinafter "water-filled pores" 110*a*) and pores 110 filled with hydrocarbons (hereinafter "hydrocarbon-filled pores" 110*b*). The hydrocarbons within the hydrocarbon-filled pores 110*b* may be free hydrocarbons, bound hydrocarbons, or a mixture thereof. Free hydrocarbons may flow under normal hydrocarbon reservoir production conditions. Bound hydrocarbons are hydrocarbons bound to grain surfaces by chemical and/or capillary forces and may not flow under normal hydrocarbon reservoir production conditions.

The concentration of hydrocarbons within the fluid-filled rock 115 may be controlled by the structural properties of the fluid-filled rock 115 such as, but not limited to, the size, shape, density, degree of connection, and packing of both the grains 105 and pores 110. Further, the concentration of hydrocarbons within, and the structural properties of, the fluid-filled rock 115 may control various porosities of the fluid-filled rock 115. In the context of this disclosure, the various porosities may include, but are not limited to, total porosity, total hydrocarbon-filled porosity, and hydrocarbon-filled porosity. Total porosity is defined as the fraction of the volume of the rock 100 that is occupied by the pores 110 no matter the type of fluid that fills the pores 110. Total hydrocarbon-filled porosity is defined as the fraction of the volume of the rock 100 that is occupied by the pores 110 filled with hydrocarbons where the rock 100 is in situ rock within a subterranean region of interest. Hydrocarbon-filled porosity is defined as the fraction of the volume of the rock 100 that is occupied by the pores 110 filled with hydrocarbons where the rock 100 is an ex situ rock sample extracted from the subterranean region of interest. In some embodiments, a portion or all of the free hydrocarbons within the ex situ rock sample (hereinafter simply "rock sample") may have volatilized following extraction from the subterranean region of interest. As such, a hydrocarbon-filled porosity for a rock sample may be less than a total hydrocarbon-filled porosity for the rock sample if the rock sample were in situ.

Permeability may be closely related to porosity. Permeability is a measure of how easily fluid flows through the fluid-filled rock 115. The degree of connection between the pores 110 and the viscosity of the fluid filling the pores 110 may constrain permeability, at least in part. As such, permeability may affect, at least in part, what hydrocarbons are free and what hydrocarbons are bound.

Figure 2:
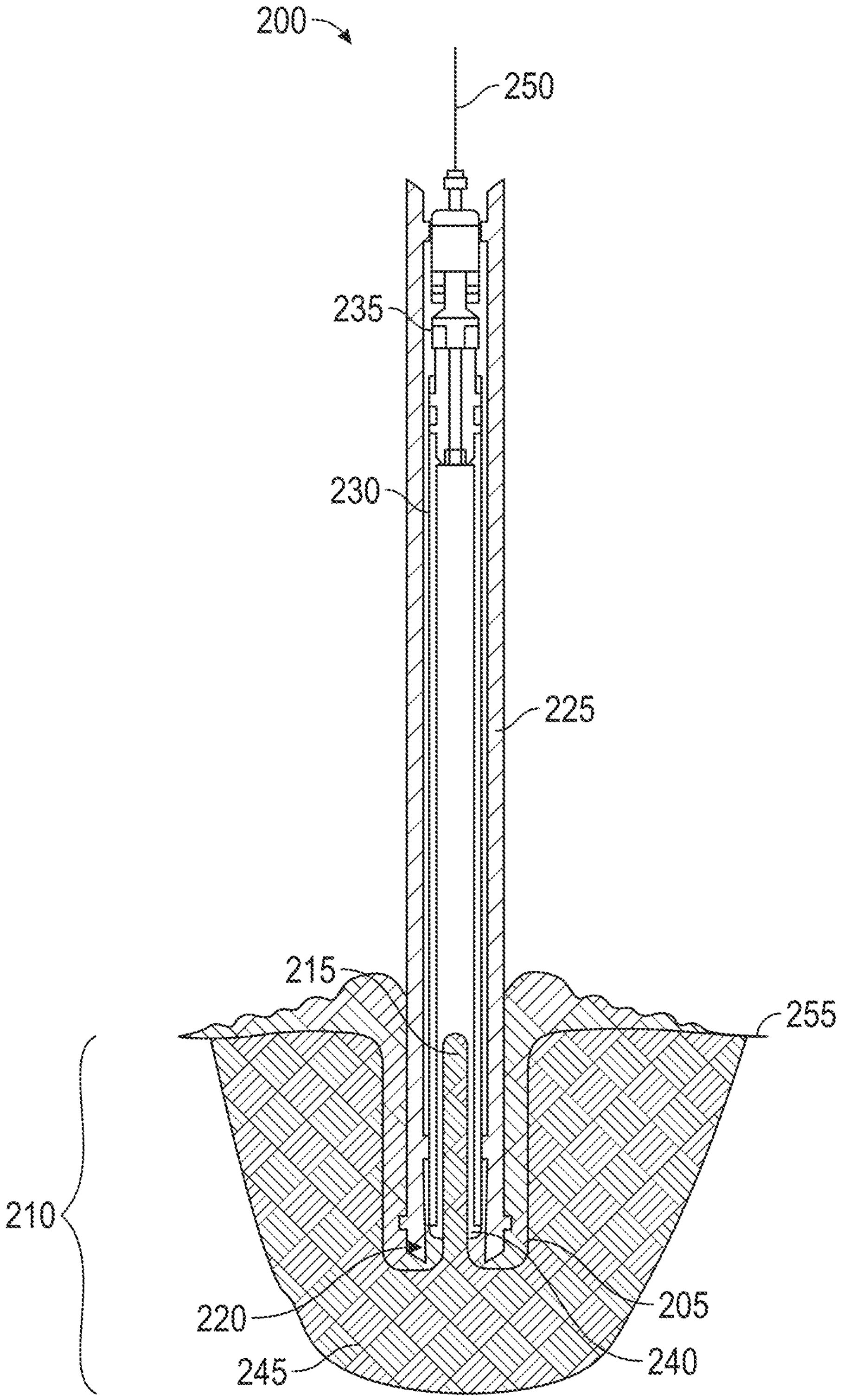
FIG. 2 illustrates a rock coring system in accordance with one or more embodiments.

In some embodiments, the hydrocarbon-filled porosity for a fluid-filled rock 115 may be determined by nuclear magnetic resonance (NMR) testing a rock sample in a laboratory setting. Rock samples may be obtained from a subterranean region of interest using a rock coring system. FIG. 2 illustrates a rock coring system 200 in accordance with one or more embodiments. The rock coring system 200 is configured to simultaneously drill the well 205 within a subterranean region of interest 210 and retrieve one or more ex situ rock cores 215 (hereinafter simply "rock cores") along an interval of the well 205. As such, the rock coring system 200 may be considered part of a drilling system. The rock coring system 200 may collect rock cores 215 continuously or at intervals while drilling the well 205. To do so, the rock coring system 200 may include a coring bit 220 attached to a core barrel 225. Within the core barrel 225, an inner barrel 230 is disposed between a swivel 235 attached to an upper portion of the core barrel 225 and a core catcher 240 is disposed close to the coring bit 220. The coring bit 220 consists of an annular cutting or grinding surface configured to flake, gouge, grind, or wear away the in situ rock 245 within the subterranean region of interest 210 at the base or "toe" of the well 205. A central axial orifice is configured to allow a cylindrical rock core 215 to pass through. The annular cutting surface of the coring bit 220 typically includes embedded polycrystalline compact diamond (PDC) cutting elements.

The inner barrel 230 within the core barrel 225 may be disposed above or behind the coring bit 220. Further, the inner barrel 230 may be separated from the coring bit 220 by the core catcher 240. As the coring bit 220 grinds away the in situ rock 245 within the subterranean region of interest 210, the cylindrical rock core 215 passes through the central orifice of the coring bit 220 and through the core catcher 240 into the inner barrel 230 as the coring bit 220 advances deeper into the subterranean region of interest 210. The inner barrel 230 may be attached by the swivel 235 to the remainder of the core barrel 225 to permit the inner barrel 230 to remain stationary as the core barrel 225 rotates together with the coring bit 220. When the inner barrel 230 is filled with the rock core 215, the core barrel 225 containing the rock core 215 may be raised and retrieved at the surface of the earth 255. The core catcher 240 serves to grip the bottom of the rock core 215 and, as lifting tension is applied to the drillstring 250 and the core barrel 225, the rock core 215 breaks away from the undrilled in situ rock 245 within subterranean region of interest 210 below it. The core catcher 240 may retain the rock core 215 so that it does not fall out the bottom of the core barrel 225 through the annular orifice of the coring bit 220 as the core barrel 225 is raised to the surface of the earth 255.

In addition to collecting rock cores 215 while drilling the well 205, smaller "sidewall rock cores" may be obtained after drilling a portion or all of the well 205. A sidewall rock coring system (not shown) may be lowered by wireline into the well 205. When deployed, the sidewall rock coring system presses or clamps itself against the wall of the well 205 and a sidewall rock core is obtained either by drilling into the wall of the well 205 with a hollow drill bit or by firing a hollow bullet into the wall of the well 205 using an explosive charge. More than 50 such sidewall rock cores may be obtained during a single deployment of a sidewall rock coring system into the well 205. Hereinafter, the term "rock coring system" is the rock coring system 200 as illustrated in FIG. 2, the sidewall rock coring system, or both. Further, the term "rock cores" is used to describe the rock cores 215 obtained using either the rock coring system 200 as illustrated in FIG. 2 or the sidewall rock coring system.

In general, the rock cores 215 may be collected along any interval of the well 205. As such, rock cores 215 may be collected along an interval of the well 205 that intersects a hydrocarbon reservoir within the subterranean region of interest 210. These rock cores 215 may contain hydrocarbons, some of which may be free hydrocarbons, bound hydrocarbons, or a combination thereof.

Under ideal circumstances, each rock core 215 is recovered as a single, continuous, intact cylinder of rock. However, frequently, each rock core 215 takes the form of several shorter cylindrical segments separated by breaks. The breaks may be a consequence of stresses experienced by each rock core 215 during coring or may be caused by pre-existing vugs, channels, and/or fractures within the subterranean region of interest 210.

Unless special precautions are taken, when a rock core 215 reaches the surface of the earth 255, some-to-all of the free hydrocarbons within the rock core 215 may volatilize as these free hydrocarbons may be below bubblepoint at surface temperatures and pressures. As such, the concentration of hydrocarbons within the rock core 215 may be less than the in situ concentration of hydrocarbons within the in situ rock 245 from which the rock core 215 was extracted.

In general, each rock core 215 may be up to 15 centimeters in diameter and approximately ten meters long. To prepare a rock core 215 for NMR testing in the laboratory setting, each rock core 215 may be cut into multiple rock samples (e.g., core plugs). Each rock sample may be in the shape of a cylinder (e.g., disc) or cuboid where each dimension is on the order of centimeters, though other shapes and dimensions may be used. Further, each rock sample may be cut along a particular axis of the well 205, such as parallel or perpendicular to the well 205.

In the laboratory setting, each rock sample may be NMR tested using a laboratory NMR system. FIG. 3A illustrates a laboratory NMR system 300 in accordance with one or more embodiments. In the context of this disclosure, NMR analysis may include the process of polarizing certain atoms within a rock sample 302 using a magnetic field and measuring the time it takes for the atoms to return to an equilibrium state after the magnetic field is removed. In some embodiments, the laboratory NMR system 300 may include a detection region 305 within a wire coil 310 where the rock sample 302 may be placed. The wire coil 310 may reside within a magnet 315 or between a pair of magnets 315. The magnet(s) 315 may induce a static or oscillating magnetic field 320 (e.g., radio frequency (RF) waves) through the detection region 305 (and in turn the rock sample 302) as prescribed by a magnet controller 322. The response (i.e., the NMR signal) of the rock sample 302 to the induced magnetic field 320 may be measured by a detector 325 and transferred to, stored on, and/or processed using a computer system 330. Such a computer system 330 is described in detail relative to FIG. 11.

Prior to induction of the magnetic field 320, the rock sample 302 may consist of atoms at an initial equilibrium state. However, following the induction of the magnetic field 320, the nuclei of some of the atoms that make up the rock sample 302 may become excited and behave like small magnets. If a broad spectrum of RF waves and/or one or more RF pulses are applied to the rock sample 302 using the magnetic field 320, the excited nuclei may oscillate at their resonant frequencies. This process may be referred to as magnetic resonance. When the RF waves or RF pulse are switched off, the excited nuclei return to their initial equilibrium state or "relax" over time.

"Relaxation times" may be recorded based on the time it takes for the excited nuclei to return to their initial equilibrium states. Relaxation times may take the form of a distribution over time, typically from 0.3 milliseconds (ms) to 3 seconds(s). Further, relaxation times may be associated with a longitudinal axis and transverse axis of the magnetic field 320. As such, the laboratory NMR system 300 may detect and record longitudinal relaxation times T1 and transverse relaxation times T2. A laboratory NMR system 300 that determines both longitudinal relaxation times T1 and transverse relaxation times T2 may be referred to as a two-dimensional NMR system. In some embodiments, the longitudinal relaxation times T1 and transverse relaxation times T2 may be displayed in the form of an NMR output.

Figure 3B:
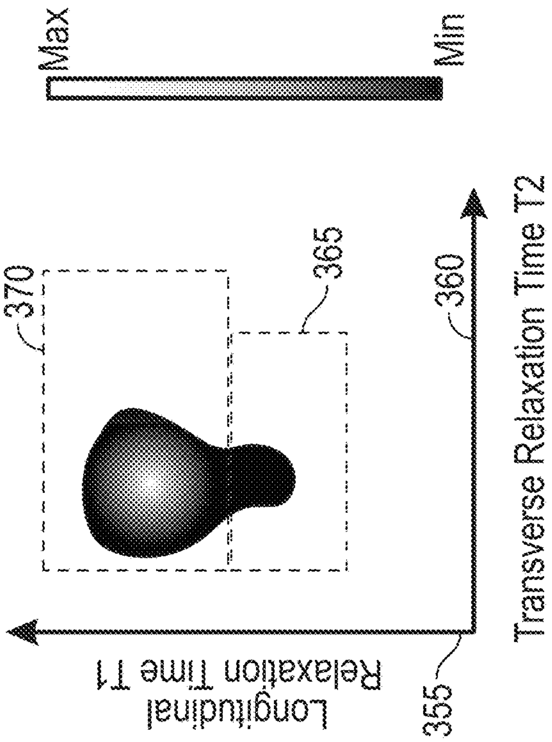
FIG. 3B displays an NMR output in accordance with one or more embodiments.
Figure 3A:
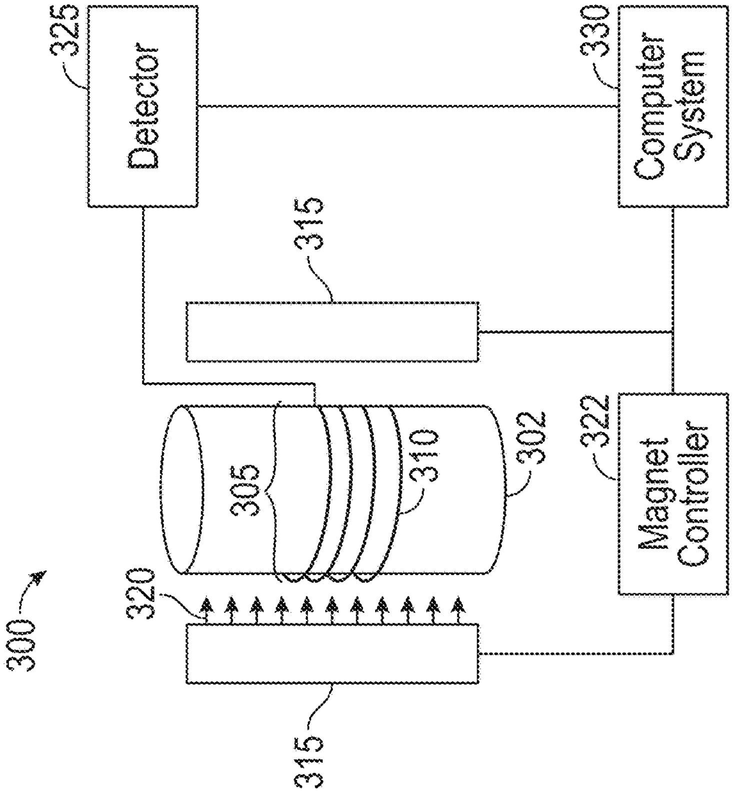
FIG. 3A illustrates a laboratory nuclear magnetic resonance (NMR) system in accordance with one or more embodiments.

FIG. 3B displays an NMR output 350 in accordance with one or more embodiments. The NMR output 350 may include the longitudinal relaxation times T1 of the excited nuclei as shown along the ordinate 355. The NMR output 350 may further include the transverse relaxation times T2 of the excited nuclei as shown along the abscissa 360.

The NMR output 350 may be separated into regions such as a water region 365 and hydrocarbon region 370 based on previously-determined cutoffs. The hydrocarbon region 370 may be characterized by an excited portion and decay portion separated by a peak amplitude 375. The peak amplitude 375 may be proportional and calibrated to porosity units (p.u.) to determine hydrocarbon-filled porosity of the rock sample 302.

Figure 4A:
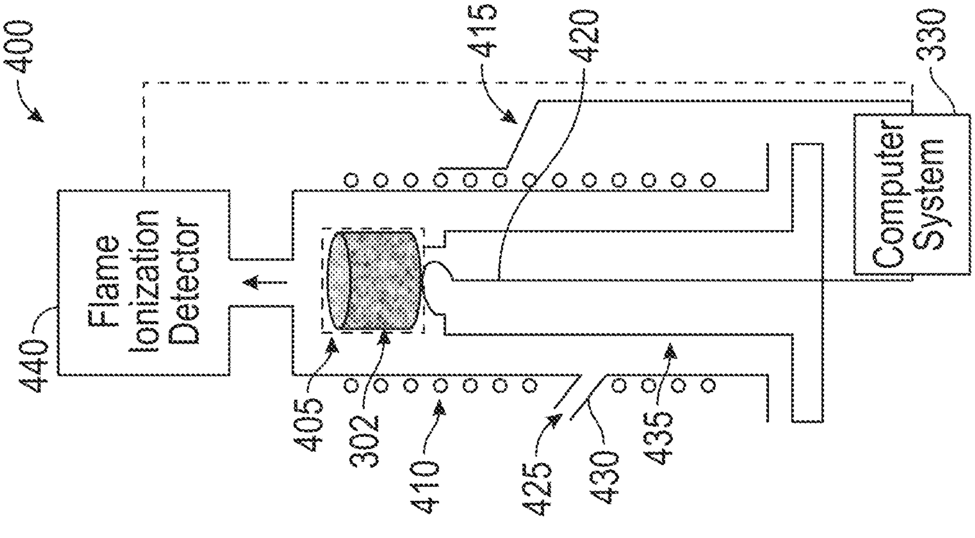
FIG. 4A illustrates a pyrolysis system in accordance with one or more embodiments.

Following NMR testing of the rock sample 302 to determine the hydrocarbon-filled porosity, the rock sample 302 may be pyrolysis tested using a pyrolysis system. FIG. 4A illustrates a pyrolysis system 400 in accordance with one or more embodiments. Pyrolysis may be the process of thermally decomposing and analyzing the constituents of the rock sample 302. The pyrolysis system 400 may be an open or closed system. For example, the pyrolysis system 400 may perform a pyrolysis test in an inert atmosphere (i.e., in the absence of oxygen). Pyrolysis and/or pyrolysis systems 400 may be referred to as Rock-Eval (e.g., Rock-Eval 6 and Rock-Eval 7), SR Analyzer, HAWK, POPI-TOC, and Pyromat.

While FIG. 4 illustrates pyrolysis, features and processes illustrated in and discussed relative to FIG. 4 are not meant to limit the present disclosure. Further, the discussion of the pyrolysis system 400 herein focuses on the use of the pyrolysis system 400 in the context of this disclosure. A person of ordinary skill in the art will appreciate that the pyrolysis system 400 may include other features and other functions not discussed herein configured to further characterize the rock sample 302 by thermally decomposing the rock sample 302 into its constituents.

The rock sample 302 may be loaded into a crucible 405. The crucible 405 may then be loaded into a furnace 410. During a pyrolysis test, the furnace 410 may heat the rock sample 302 based on a prescribed temperature profile. To ensure the prescribed temperature profile is maintained during the pyrolysis test, a first thermocouple 415 may measure the temperature of the furnace 410 during the pyrolysis test based on a first pre-determined sampling rate. The temperatures measured by the first thermocouple 415 may be sent to a computer system 330 to be used as feedback. A second thermocouple 420 may measure the temperature of the rock sample 302 during the pyrolysis test based on a second pre-determined sampling rate. The temperatures measured by the second thermocouple 420 may also be sent to the computer system 330. In some embodiments, to ensure the rock sample 302 is maintained in an inert atmosphere during the pyrolysis test, nitrogen 425 or other inert gas may be injected into the pyrolysis system 400 via an opening 430.

As the furnace 410 heats the rock sample 302 based on the prescribed temperature profile during the pyrolysis test, constituents of the rock sample 302 volatilize or pyrolyze at discrete times and discrete temperatures as pyrolysate. In some embodiments, the hydrocarbons within the rock sample 302 may volatilize first. The kerogen within the rock sample 302 may volatilize and pyrolyze second. The carbon dioxide ($CO_2$) within the rock sample 302 may pyrolyze third. A piston 435 may direct one or more of each volatilized or pyrolyzed constituent towards a flame ionization detector (FID) 440 where each volatilized or pyrolyzed constituent is detected. The detected FID signals may be converted to electrical signals and transferred to and stored on the computer system 330. The computer system 330 may determine the concentration of pyrolyzed constituents relative to time (hereinafter "concentration data") based, at least in part, on the electrical signals.

Figure 4B:
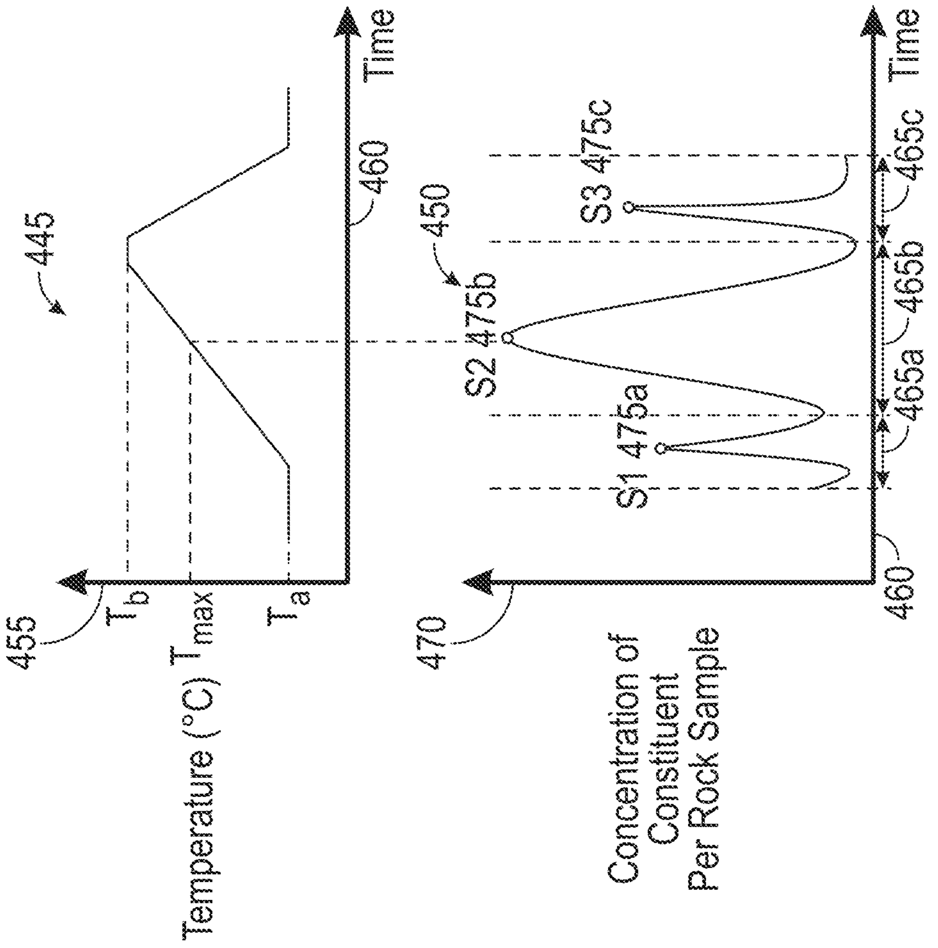
FIG. 4B displays a prescribed temperature profile and concentration data in accordance with one or more embodiments.

FIG. 4B displays a prescribed temperature profile 445 and concentration data 450 in accordance with one or more embodiments. The prescribed temperature profile 445 may prescribe at what time what temperature is applied to the furnace 410 or the rock sample 302 during pyrolysis testing within the pyrolysis system 400. Temperature is shown along the ordinate 455. Time is shown along the abscissa 460. In some embodiments, the prescribed temperature profile 445 may prescribe a rise, hold, and decline profile where $T_a$ may be approximately 100° C. and $T_b$ may be approximately 650° C. Subjecting the rock sample 302 to the prescribed temperature profile 445 may volatilize or pyrolyze each of the constituents of the rock sample 302 over discrete time windows 365*a-c* as displayed within the concentration data 450.

The concentration data 450 displays the volatilization or pyrolyzation of three constituents of the rock sample 302. The concentration data 450 displays the concentration of each constituent per rock sample 302, as shown along the ordinate 470, typically in units of milligrams per gram. The concentration data 450 further displays the time at which each constituent of the rock sample 302 volatilized or pyrolyzed as shown along the abscissa 460. During the pyrolysis test, the hydrocarbons within the rock sample 302 (i.e., the first constituent) may volatilize during the first time window 465*a* where the peak concentration of hydrocarbons volatilize at S1 475*a*. Hereinafter, the term "concentration of hydrocarbons" is considered synonymous to the concentration at S1 385*a* and is denoted "concentration of hydrocarbons S1." However, a person of ordinary skill in the art will appreciate that S1 may be referred to as "concentration of free hydrocarbons" or simply "free hydrocarbons" in the field of endeavor. In the context of this disclosure, the rock sample 302 contains bound hydrocarbons and little-to-no free hydrocarbons and is why S1 is simply referred to as "concentration of hydrocarbons." Returning to FIG. 4B, kerogen within the rock sample 302 (i.e., the second constituent) may pyrolyze during the second time window 465*b* where the peak concentration of kerogen pyrolyzes at S2 475*b*. Carbon dioxide ($CO_2$) (i.e., the third constituent) may pyrolyze during the third time window 465*c* where the peak concentration of $CO_2$ pyrolyzes at S3 475*c*.

The process of NMR testing and pyrolysis testing a rock sample 302 in series may be repeated for each of multiple rock samples 302. The hydrocarbon-filled porosity and concentration of hydrocarbons S1 determined for each rock sample 302 may then be used to determine a relationship.

Figure 5:
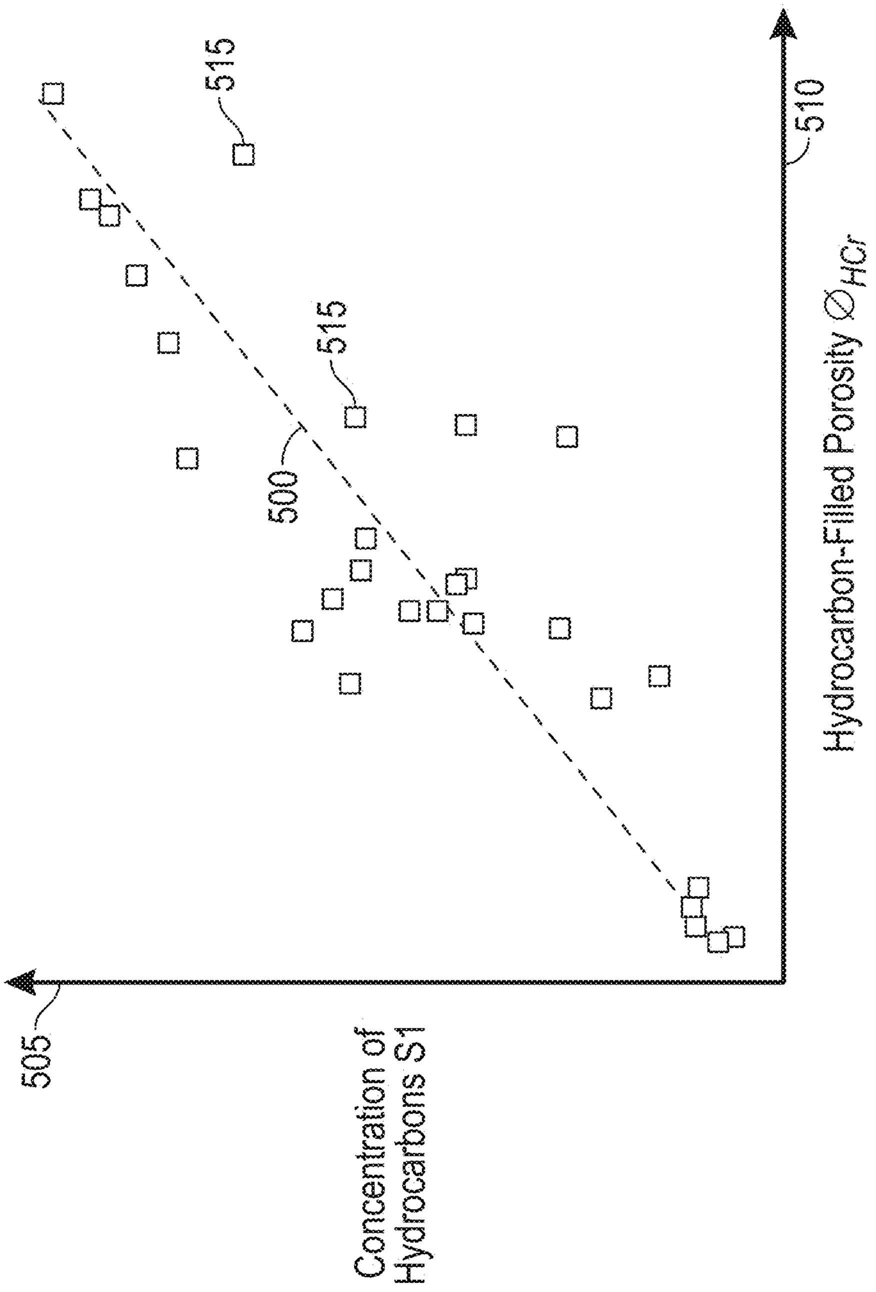
FIG. 5 displays a relationship in accordance with one or more embodiments.

FIG. 5 displays a relationship 500 in accordance with one or more embodiments. The concentration of hydrocarbons S1 determined from pyrolysis testing is shown along the ordinate 505. The hydrocarbon-filled porosity $Ø_{HCr}$ determined from NMR testing is shown along the abscissa 510. Each point 515 in FIG. 5 is associated with the hydrocarbon-filled porosity $Ø_{HCr}$ and the concentration of hydrocarbons S1 determined for one rock sample 302.

The relationship 500 may be obtained by applying regression analysis to the points 515. In some embodiments, the relationship 500 may be a linear relationship as FIG. 5 displays. The linear relationship may take the form:

$$S1 = a * Ø_{HCr} + b, \quad \text{Equation (1)}$$

where a and b are constants. In other embodiments, the relationship 500 may be, but is not limited to, a polynomial relationship, exponential relationship, logarithm relationship, or power relationship. Thus, the relationship 500 may relate hydrocarbon-filled porosity $Ø_{HCr}$ and concentration of hydrocarbons S1 such that one may be determined from the other using the relationship 500.

Figure 6A:
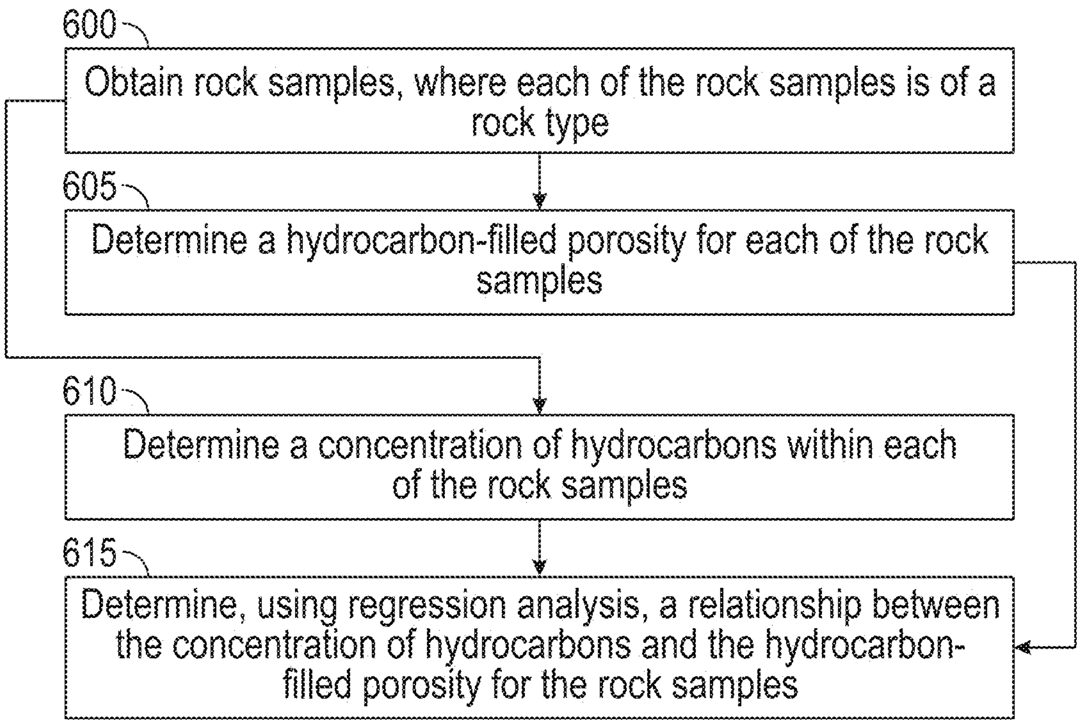
FIG. 6A describes a method in accordance with one or more embodiments.

FIG. 6A describes a method to determine the relationship 500 in accordance with one or more embodiments. In step 600, rock samples 302 are obtained from a rock coring system 200. Each of the rock samples 302 is of a rock type. The rock samples 302 may be obtained from one or more subterranean regions of interest 210. Further, each of the rock samples 302 may be filled with free hydrocarbons, bound hydrocarbons, or a combination thereof.

In step 605, a hydrocarbon-filled porosity $Ø_{HCr}$ is determined for each of the rock samples 302 using a laboratory NMR system 300 as previously described.

In step 610, a concentration of hydrocarbons S1 is determined for each of the rock samples 302 using a pyrolysis system 400 as previously described. Steps 605 and 610 may be performed in series for each rock sample 302 one at a time.

In step 615, the relationship 500 between the concentration of hydrocarbons S1 determined in step 610 and the hydrocarbon-filled porosity $Ø_{HCr}$ determined in step 605 for the rock samples 302 is determined using regression analysis. In some embodiments, the relationship 500 is a linear relationship. In some embodiments, the relationship may be determined using a computer system 330.

Figure 6B:
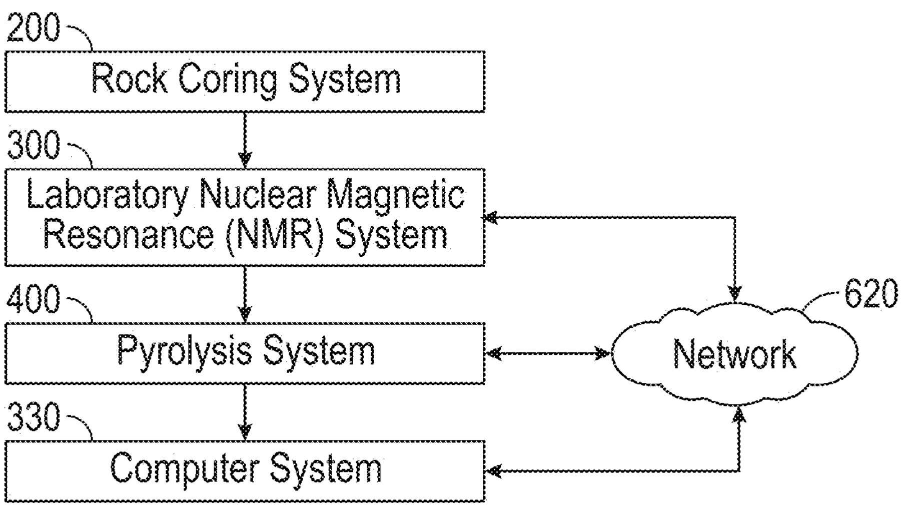
FIG. 6B shows a flowchart of systems in accordance with one or more embodiments.

FIG. 6B illustrates systems associated with the method described in FIG. 6A in accordance with one or more embodiments. The rock coring system 200 described relative to FIG. 2 may be configured to obtain the rock samples 302 as described in step 600 of FIG. 6A. Specifically, the rock coring system 200 may extract one or more rock cores 215. The one or more rock cores 215 may be sealed, transported, and stored in a laboratory setting. In the laboratory setting, the one or more rock cores 215 may be unsealed, cut and ground into one or more rock samples 302, and re-sealed.

Each rock sample 302 may be NMR tested in the laboratory NMR system 300 as described relative to FIG. 3A. The laboratory NMR system 300 may be a two-dimensional NMR system that is configured to determine longitudinal relaxation times T1 and transverse relaxation times T2 as displayed as the NMR output 350 in FIG. 3B. The laboratory NMR system 300 may be communicably coupled to a computer system 330 via a network 620. As such, the longitudinal relaxation times T1 and transverse relaxation times T2 determined for each rock sample 302 may be transferred to and stored on the computer system 330 via the network 620. In some embodiments, the computer system 330 may be configured to determine the hydrocarbon-filled porosity $Ø_{HCr}$ for each rock sample 302 as described in step 605 of FIG. 6A using the peak amplitude 375 within the hydrocarbon region 370 of the NMR output 350 as previously described relative to FIG. 3B.

Following NMR testing, each rock sample 302 may be pyrolysis tested in the pyrolysis system 400 as described relative to FIG. 4. In some embodiments, each rock sample 302 may be immediately pyrolysis tested following NMR testing. In other embodiments, each rock sample 302 may be re-sealed between NMR testing and pyrolysis testing. The pyrolysis system 400 may be configured to determine the concentration of hydrocarbons S1 for each rock sample 302 as described in step 610 of FIG. 6A and displayed in FIG. 4B. The pyrolysis system 400 may be communicably coupled to the computer system 330 via the network 620. As such, the concentration of hydrocarbons S1 for each rock sample 302 may be transferred to and stored on the computer system 330 via the network 620.

The computer system 330 may be configured to determine the relationship 500 using the concentration of hydrocarbons S1 and the hydrocarbon-filled porosity $Ø_{HCr}$ determined for each rock sample 302 using regression analysis as described in step 615 in FIG. 6A.

Figure 7:
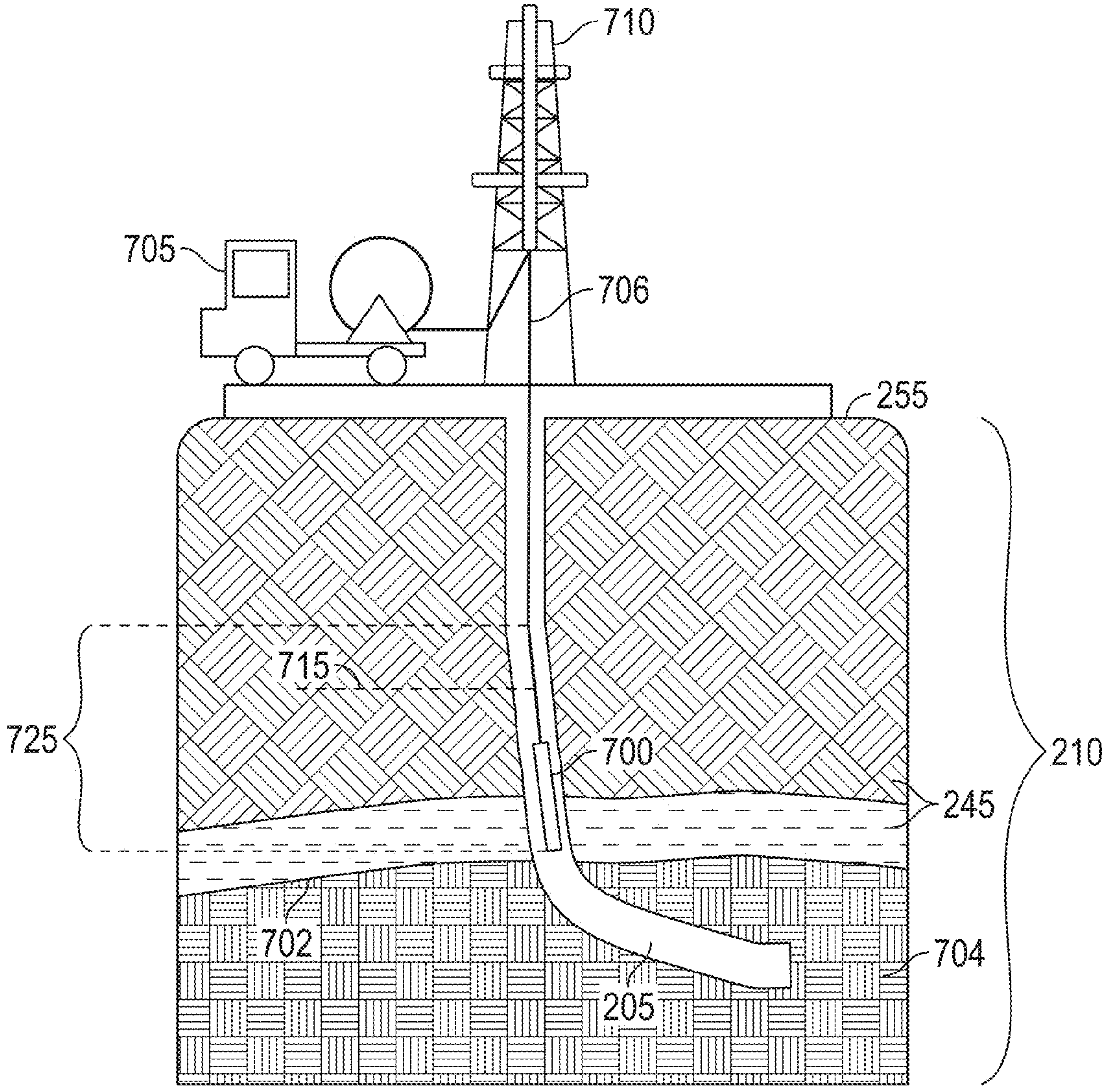
FIG. 7 illustrates a well logging system downhole in accordance with one or more embodiments.

FIG. 7 illustrates a well logging system 700 downhole in a well 205 in accordance with one or more embodiments. Prior to deploying the well logging system 700 downhole, the well 205 may be partially or completely drilled within a subterranean region of interest 210 using the rock coring system 200 as previously described relative to FIG. 2 or a separate drilling system (not shown). The well 205 may traverse layers of in situ rock 245 separated by geological boundaries 702 and/or other structural features before ultimately penetrating a hydrocarbon reservoir 704. In some embodiments, the well logging system 700 may be lowered into the well 205 following the removal of the rock coring system 200 or separate drilling system. The well logging system 700 may be supported by a truck 705 and derrick 710 above ground. For example, the truck 705 may carry a conveyance mechanism 706 used to lower the well logging system 700 into the well 205. The conveyance mechanism 706 may be used to lower the well logging system 700 into the well 205. The conveyance mechanism 706 may be a wireline, coiled tubing, or drillpipe that may include means to provide power to the well logging system 700 and a telemetry channel from the well logging system 700 to the surface of the earth 255. In some embodiments, the well logging system 700 may be translated along the well 205 to acquire a well log over an interval 725 of the well 205. Each in situ rock 245 that the well 205 penetrates may be positioned at a discrete depth 715 within the interval 725.

The well logging system 700 used to collect the well logs over the interval 725 may be, but is not limited to, an acoustic logging tool (which may be a sonic logging tool), density logging tool, neutron porosity logging tool, resistivity logging tool, and NMR logging tool. As such, the well logs may include, but are not limited to, an acoustic log (which may be a sonic log), density log, neutron porosity log, resistivity log, NMR log, and any combination or derivation thereof.

Well logs may be used, at least in part, to determine the total hydrocarbon-filled porosity $Ø_{HC}$ for an in situ rock 245 at a discrete depth 715. In some embodiments, the total hydrocarbon-filled porosity $Ø_{HC}$ of in situ rock 245 at a discrete depth 715 may be determined by:

$$Ø_{HC} = (1 - SW) * Ø_t, \quad \text{Equation (2)}$$

where SW is water saturation at the discrete depth 715 and $Ø_t$ is total porosity at the discrete depth 715. In some embodiments, water saturation SW at the discrete depth 715 may be determined from a resistivity log. In some embodiments, total porosity $Ø_t$ at the discrete depth 715 may be determined from a neutron porosity log, density log, sonic log, or NMR log. A person of ordinary skill in the art will appreciate that any log may be corrected and/or calibrated using data collected from rock cores 215.

Keeping with Equation (2), a person of ordinary skill in the art will appreciate that the compliment of water saturation SW (i.e., (1−SW)) may be considered hydrocarbon saturation. A person of ordinary skill in the art will also appreciate that other models may be used in place of Equation (2) and/or in addition to Equation (2) to ultimately determine the total hydrocarbon-filled porosity $Ø_{HC}$.

The total hydrocarbon-filled porosity $Ø_{HC}$ and the relationship 500 may then be used to determine an in situ concentration of hydrocarbons $S1_c$ within the in situ rock 245 or to correct the concentration of hydrocarbons S1 within a rock sample 302. To do so, the total hydrocarbon-filled porosity $Ø_{HC}$ may replace the hydrocarbon-filled porosity $Ø_{HCr}$ in Equation (1) such that:

$$S1_c = a * Ø_{HC} + b, \quad \text{Equation (3)}$$

to determine the in situ concentration of hydrocarbons $S1_c$ within the in situ rock 245. A person of ordinary skill in the art will appreciate that the in situ concentration of hydrocarbons $S1_c$ may be a reasonable estimate of the concentration of hydrocarbons S1 unaffected by free hydrocarbon losses.

FIG. 8A describes a method to determine the in situ concentration of hydrocarbons $S1_c$ within an in situ rock 245 in accordance with one or more embodiments. In step 800, well logs are obtained along an interval 725 of a well 205 located within a subterranean region of interest 210. The well logs may be obtained from the well logging system 700 as described relative to FIG. 7. The well 205 penetrates the in situ rock 245 at a discrete depth 715 within the interval 725. Further, the in situ rock 245 is of a rock type as previously described. In some embodiments, the well logs may include a resistivity log among other logs.

In step 805, a total hydrocarbon-filled porosity $Ø_{HC}$ is determined for the in situ rock 245 using, at least in part, the well logs. In some embodiments, a water saturation SW at the discrete depth 715 may be determined from the resistivity log. In some embodiments, a total porosity $Ø_t$ at the discrete depth 715 may be determined from a neutron porosity log. In some embodiments, the water saturation SW and total porosity $Ø_t$ at the discrete depth 715 may be input into Equation (2) to determine the total hydrocarbon-filled porosity $Ø_{HC}$ for the in situ rock 245.

In step 810, a relationship 500 is obtained between a concentration of hydrocarbons S1 and a hydrocarbon-filled porosity $Ø_{HCr}$ for the rock type. In some embodiments, the relationship 500 may be determined as previously described relative to FIG. 6A. In some embodiments, the relationship 500 may be a linear relationship.

In step 815, the in situ concentration of hydrocarbons S1, within the in situ rock 245 is determined using the relationship 500 obtained in step 810 and the total hydrocarbon-filled porosity $Ø_{HC}$ determined in step 805. To do so, the total hydrocarbon-filled porosity $Ø_{HC}$ may be input into Equation (3) to determine the in situ concentration of hydrocarbons $S1_c$ as the constants a and b are previously determined as the relationship 500.

In step 820, a recovery factor is determined for the in situ rock 245. In the context of this disclosure, the term "recovery factor" may be synonymous to the amount of hydrocarbons that may be produced from a hydrocarbon reservoir 704. The recovery factor may take the form of a productivity index. The recovery factor may be based, at least in part, on the in situ concentration of hydrocarbon S1c determined in step 815. In some embodiments, the recovery factor may be a value of a recoverable volume of hydrocarbons initially in place within the hydrocarbon reservoir 704 that includes the in situ rock 245.

In step 825, a hydrocarbon production rate is determined based, at least in part, on the recovery factor determined in step 820. In some embodiments, the hydrocarbon production rate may be the volume of hydrocarbons produced from the hydrocarbon reservoir 704 over a unit of time, which may be the lifetime of the well 205 that penetrates the hydrocarbon reservoir 704.

In step 830, a production management plan is designed based, at least in part, on the hydrocarbon production rate determined in step 825. In the context of this disclosure, the production management plan may define and organize the activities associated with producing the hydrocarbons from the hydrocarbon reservoir 704. For example, the production management plan may define how rapidly to produce the hydrocarbons for various time intervals from the well 205 over the lifetime of the well 205. Producing the hydrocarbons from the hydrocarbon reservoir 704 may be referred to as primary recovery. The production management plan may also define when and where to drill new wells 205 and how to complete the new wells 205 that penetrate the hydrocarbon reservoir 704 to further produce hydrocarbons. Further, the production management plan may define when, where, and how to stimulate existing and new wells 205, such as during secondary and/or tertiary recovery. Further still, the production management plan may define when to abandon each well 205.

FIG. 8B illustrates systems associated with the method described in FIG. 8A in accordance with one or more embodiments. The well logging system 700 as described relative to FIG. 7 may be configured to collect the well logs as described in step 800 of FIG. 8A. The computer system 330 may receive the well logs from the well logging system 700. The computer system 330 may be configured to perform steps 800, 805, 810, 815, and 820 of FIG. 8A to ultimately determine the recovery factor. The production management system 840 may receive the recovery factor. Further, the production management system 840 may perform steps 825 and 830 to ultimately design the production management plan. In some embodiments, the production management system 840 may be stored on a memory of the computer system 330.

Figure 9:
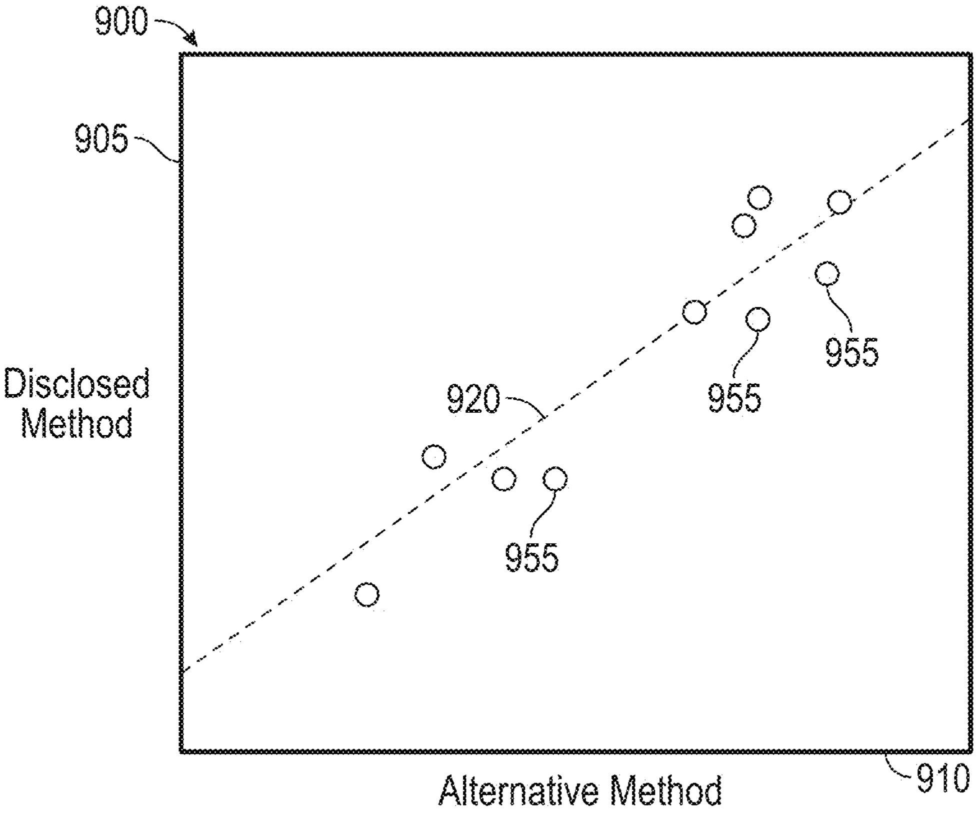
FIG. 9 displays a comparison of in situ concentrations of hydrocarbons in accordance with one or more embodiments.

FIG. 9 displays a comparison of in situ concentrations of hydrocarbons 900 in accordance with one or more embodiments. The in situ concentrations of hydrocarbons 900 determined using the disclosed method are displayed along the ordinate 905. The in situ concentrations of hydrocarbons

900 determined using an alternative method are displayed along the abscissa 910. Each comparison point 915 is displayed relative to a correlation 920. The correlation 920 is a one-to-one correlation that may be written as x=y. As such, FIG. 9 illustrates that the disclosed method determines similar in situ concentrations of hydrocarbons 900 relative to the alternative method.

Figure 10:
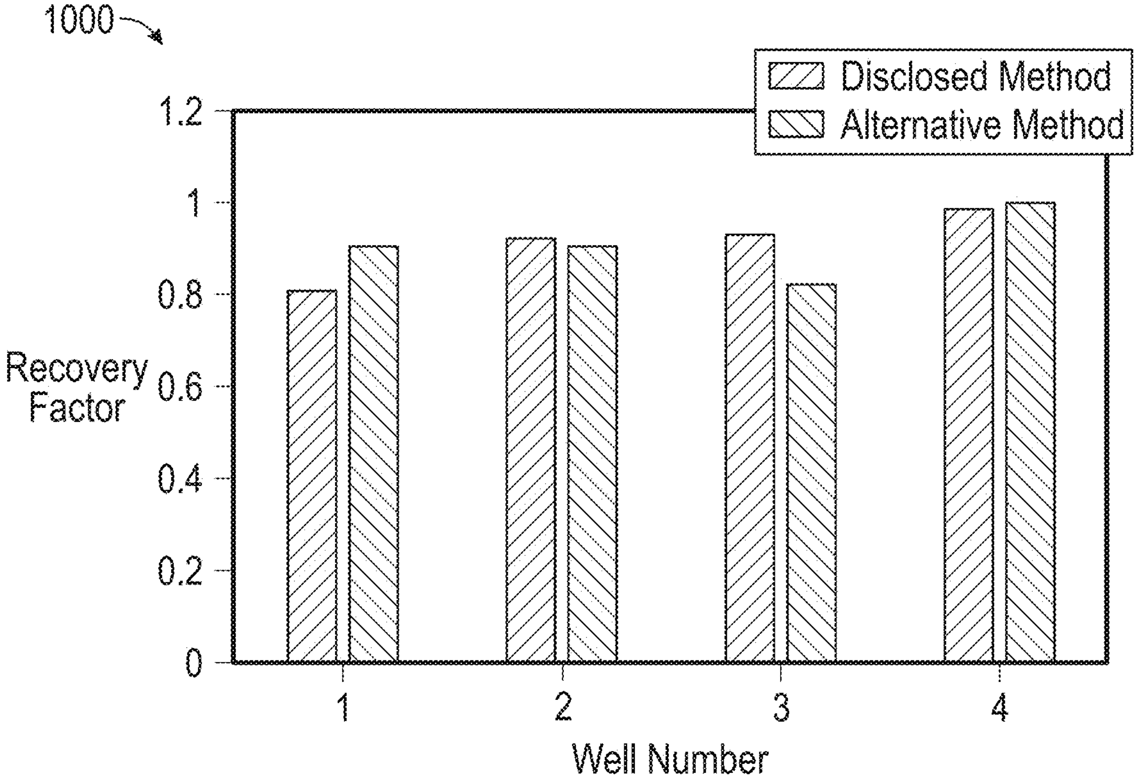
FIG. 10 displays a comparison of recovery factors in accordance with one or more embodiments.

FIG. 10 displays a comparison of recovery factors 1000 in accordance with one or more embodiments. The recovery factors 1000 determined using the disclosed method and an alternative method are illustrated using a unique pattern fill. FIG. 10 illustrates that the disclosed method determines similar recovery factors 1000 relative to the alternative method.

Figure 11:
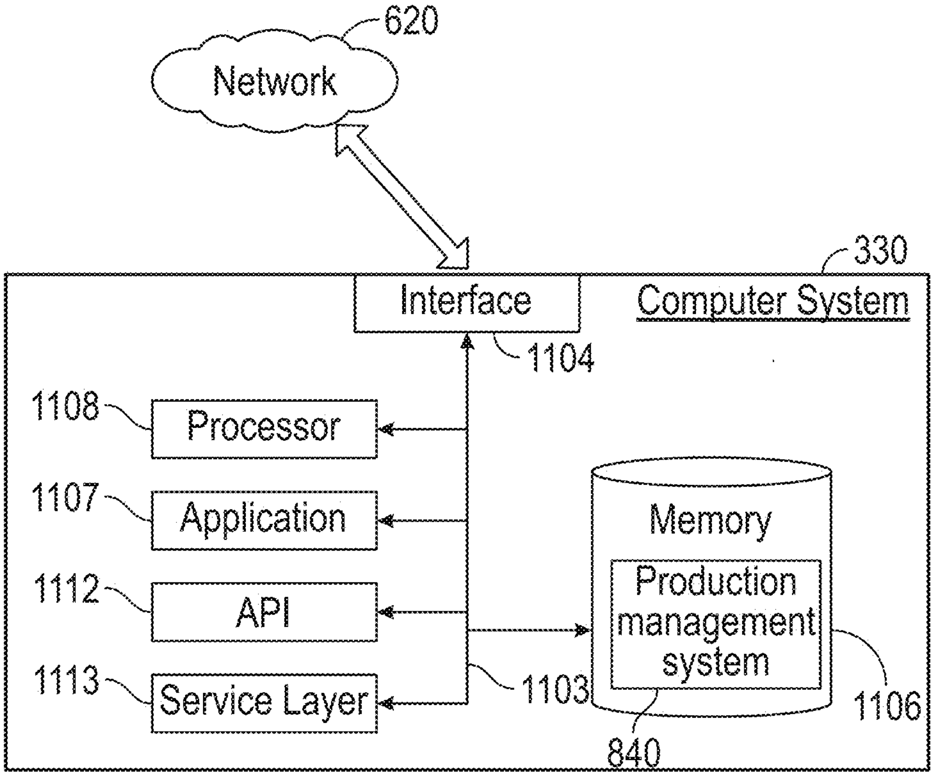
FIG. 11 illustrates a computer system in accordance with one or more embodiments.

FIG. 11 illustrates a computer system 330 in accordance with one or more embodiments. The computer system 330 may be used to provide computational functionalities associated with described algorithms, methods, functions, processes, flows, and procedures as described in this disclosure, according to one or more embodiments. The illustrated computer system 330 is intended to encompass any computing device such as a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system 330 may include a computer that includes an input device, such as a keypad, keyboard, touch screen, or other device that can accept user information, and an output device that conveys information associated with the operation of the computer system 330, including digital data, visual, or audio information (or a combination of information), or a GUI.

The computer system 330 can serve in a role as a client, network component, a server, a database or other persistency, or any other component (or a combination of roles) of a computer system for performing the subject matter described in the instant disclosure. The illustrated computer system 330 is communicably coupled with a network 620. In some implementations, one or more components of the computer system 330 may be configured to operate within environments, including cloud-computing-based, local, global, or other environment (or a combination of environments). Further, in some embodiments, the computer system 330 may be communicably coupled to the laboratory NMR system 300, pyrolysis system 400, and/or any other input or output device via the network 620.

At a high level, the computer system 330 is an electronic computing device operable to receive, transmit, process, store, or manage data and information associated with the described subject matter. According to some implementations, the computer system 330 may also include or be communicably coupled with an application server, e-mail server, web server, caching server, streaming data server, business intelligence (BI) server, or other server (or a combination of servers).

The computer system 330 can receive requests over network 620 from a client application (for example, executing on another computer system 330) and responding to the received requests by processing the said requests in an appropriate software application. In addition, requests may also be sent to the computer system 330 from internal users (for example, from a command console or by other appropriate access method), external or third-parties, other automated applications, as well as any other appropriate entities, individuals, systems, or computers.

Each of the components of the computer system 330 can communicate using a system bus 1103. In some implementations, any or all of the components of the computer system 330, both hardware or software (or a combination of hardware and software), may interface with each other or the interface 1104 (or a combination of both) over the system bus 1103 using an application programming interface (API) 812 or a service layer 1113 (or a combination of the API 1112 and service layer 1113. The API 1112 may include specifications for routines, data structures, and object classes. The API 1112 may be either computer-language independent or dependent and refer to a complete interface, a single function, or even a set of APIs. The service layer 1113 provides software services to the computer system 330 or other components (whether or not illustrated) that are communicably coupled to the computer system 330. The functionality of the computer system 330 may be accessible for all service consumers using this service layer. Software services, such as those provided by the service layer 1113, provide reusable, defined business functionalities through a defined interface. For example, the interface may be software written in JAVA, C++, or other suitable language providing data in extensible markup language (XML) format or another suitable format. While illustrated as an integrated component of the computer system 330, alternative implementations may illustrate the API 1112 or the service layer 1113 as stand-alone components in relation to other components of the computer system 330 or other components (whether or not illustrated) that are communicably coupled to the computer system 330. Moreover, any or all parts of the API 1112 or the service layer 1113 may be implemented as child or sub-modules of another software module, enterprise application, or hardware module without departing from the scope of this disclosure.

The computer system 330 includes an interface 1104. Although illustrated as a single interface 1104 in FIG. 11, two or more interfaces 1104 may be used according to particular needs, desires, or particular implementations of the computer system 330. The interface 1104 is used by the computer system 330 for communicating with other systems in a distributed environment that are connected to the network 620. Generally, the interface 1104 includes logic encoded in software or hardware (or a combination of software and hardware) and operable to communicate with the network 620. More specifically, the interface 1104 may include software supporting one or more communication protocols associated with communications such that the network 620 or interface's hardware is operable to communicate physical signals within and outside of the illustrated computer system 330.

The computer system 330 includes at least one computer processor 1108. Although illustrated as a single computer processor 1108 in FIG. 11, two or more processors may be used according to particular needs, desires, or particular implementations of the computer system 330. Generally, the computer processor 1108 executes instructions and manipulates data to perform the operations of the computer system 330 and any algorithms, methods, functions, processes, flows, and procedures as described in the instant disclosure.

The computer system 330 also includes a memory 1106 that holds data for the computer system 330 or other components (or a combination of both) that can be connected to the network 620. For example, the memory 1106 may store the production management system 840 that may be configured to perform steps 825 and 830 as previously described relative to FIG. 8A. Although illustrated as a single memory 1106 in FIG. 11, two or more memories may be used according to particular needs, desires, or particular implementations of the computer system 330 and the described functionality. While memory 1106 is illustrated as an integral component of the computer system 330, in alternative implementations, memory 1106 can be external to the computer system 330.

The application 1107 is an algorithmic software engine providing functionality according to particular needs, desires, or particular implementations of the computer system 330, particularly with respect to functionality described in this disclosure. For example, application 1107 can serve as one or more components, modules, applications, etc. Further, although illustrated as a single application 1107, the application 1107 may be implemented as multiple applications 1107 on the computer system 330. In addition, although illustrated as integral to the computer system 330, in alternative implementations, the application 1107 can be external to the computer system 330.

There may be any number of computers 330 associated with, or external to, a computer system containing a computer system 330, wherein each computer system 330 communicates over network 620. Further, the term "client," "user," and other appropriate terminology may be used interchangeably as appropriate without departing from the scope of this disclosure. Moreover, this disclosure contemplates that many users may use one computer system 330, or that one user may use multiple computers 330.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed is:

1. A method comprising:

obtaining, from a well logging system, a plurality of well logs along an interval of a well located within a subterranean region of interest that comprises a hydrocarbon reservoir, wherein the well penetrates an in situ rock within the subterranean region of interest at a discrete depth within the interval, and wherein the in situ rock is of a rock type;

determining a total hydrocarbon-filled porosity for the in situ rock using the plurality of well logs;

obtaining a relationship between a concentration of hydrocarbons and a hydrocarbon-filled porosity for the rock type;

determining an in situ concentration of hydrocarbons within the in situ rock using the relationship and the total hydrocarbon-filled porosity;

determining a recovery factor for the in situ rock based on the in situ concentration of hydrocarbons;

using a production management system:

determining a hydrocarbon production rate based on the recovery factor, and designing a production management plan for the subterranean region of interest based on the hydrocarbon production rate; and producing hydrocarbons from the hydrocarbon reservoir based on the production management plan.

2. The method of claim 1, wherein the hydrocarbon reservoir comprises the in situ rock.

3. The method of claim 1, wherein the plurality of well logs comprises a resistivity log.

4. The method of claim 1, wherein determining the total hydrocarbon-filled porosity for the in situ rock comprises:

determining a water saturation and a total porosity for the in situ rock using the plurality of well logs; and determining the total hydrocarbon-filled porosity for the in situ rock using the water saturation and the total porosity.

5. The method of claim 1, wherein the relationship comprises a linear relationship.

6. The method of claim 1, wherein obtaining the relationship comprises:

obtaining, from a rock coring system, a plurality of rock samples, wherein each of the plurality of rock samples is of the rock type.

7. The method of claim 6, wherein the plurality of rock samples is collected from the subterranean region of interest.

8. The method of claim 6, wherein the plurality of rock samples comprises the in situ rock.

9. The method of claim 6, further comprising:

determining, using a nuclear magnetic resonance (NMR) system, the hydrocarbon-filled porosity for each of the plurality of rock samples;

determining, using a pyrolysis system, the concentration of hydrocarbons within each of the plurality of rock samples; and determining, using regression analysis, the relationship between the concentration of hydrocarbons and the hydrocarbon-filled porosity for the plurality of rock samples.

10. A system comprising:

a computer system configured to:

receive, from a well logging system, a plurality of well logs along an interval of a well located within a subterranean region of interest that comprises a hydrocarbon reservoir, wherein the well penetrates an in situ rock within the subterranean region of interest at a discrete depth within the interval, and wherein the in situ rock is of a rock type, determine a total hydrocarbon-filled porosity for the in situ rock using the plurality of well logs, receive a relationship between a concentration of hydrocarbons and a hydrocarbon-filled porosity for the rock type;

determine an in situ concentration of hydrocarbons within the in situ rock using the relationship and the total hydrocarbon-filled porosity, and determine a recovery factor for the in situ rock based on the in situ concentration of hydrocarbons;

a production management system configured to:

determine a hydrocarbon production rate based on the recovery factor, and design a production management plan based on the hydrocarbon production rate; and a production system configured to produce hydrocarbons from the hydrocarbon reservoir based on the production management plan.

11. The system of claim 10, wherein the well logging system comprises a resistivity logging system.

12. The system of claim 10, further comprising:

a rock coring system configured to obtain a plurality of rock samples, wherein each of the plurality of rock samples is of the rock type.

13. The system of claim 12, further comprising:

a nuclear magnetic resonance (NMR) system configured to determine the hydrocarbon-filled porosity for each of the plurality of rock samples; and a pyrolysis system configured to determine the concentration of hydrocarbons within each of the plurality of rock samples.

14. The system of claim 13, wherein the computer system is further configured to determine, using regression analysis, the relationship between the concentration of hydrocarbons and the hydrocarbon-filled porosity for the plurality of rock samples.

15. The system of claim 13, wherein the NMR system comprises a two-dimensional NMR system.

* * * * *